United States Patent [19]

Hintermann

[11] Patent Number: 4,687,487

[45] Date of Patent: * Aug. 18, 1987

[54] JOINT IMPLANT

[75] Inventor: Hans-Erich Hintermann, Ins, Switzerland

[73] Assignee: Association Suisse pour la Recherches Horlogere, Switzerland

[*] Notice: The portion of the term of this patent subsequent to Jun. 11, 2002 has been disclaimed.

[21] Appl. No.: 722,017

[22] Filed: Apr. 11, 1985

Related U.S. Application Data

[63] Continuation-in-part of Ser. No. 419,185, Sep. 17, 1982, Pat. No. 4,522,453, which is a continuation of Ser. No. 180,578, Aug. 25, 1980, abandoned, which is a continuation of Ser. No. 24,421, Mar. 27, 1979, abandoned.

[30] Foreign Application Priority Data

Jul. 21, 1978 [CH] Switzerland ..................... 7872/78

[51] Int. Cl.$^4$ ............................................. A61F 2/30
[52] U.S. Cl. ...................................... 623/18; 623/22
[58] Field of Search .................. 623/16, 18, 22, 23; 128/92 D, 92 C, 92 CA; 428/386, 385

[56] References Cited

U.S. PATENT DOCUMENTS

| 3,643,658 | 2/1972 | Steinemenan | 128/92 D |
| 4,263,681 | 4/1981 | Notton | 623/22 |
| 4,450,201 | 5/1984 | Brill et al. | 428/336 |
| 4,522,453 | 6/1985 | Lammer et al. | 308/3 R |

FOREIGN PATENT DOCUMENTS 2025238  1/1980  United Kingdom .................. 623/16

OTHER PUBLICATIONS

Chemical Abstracts—vol. 100, 1984 No. 39 562.

Primary Examiner—Richard J. Apley
Assistant Examiner—David J. Isabella
Attorney, Agent, or Firm—Parkhurst & Oliff

[57] ABSTRACT

The mutually sliding members of a joint implant are each coated with a hard material selected from the group consisting of titanium carbide, oxicarbide, nitride, oxinitride, carbonitride and oxicarbonitride in order to improve the sliding, wear resistance and adhesion properties of the members.

A hip joint prosthesis is provided having a socket bowl coated with titanium (oxi)nitride or titanium (oxi)carbonitride with a thickness of from 2 to 3 microns and an articular head coated with titanium (oxi)carbide or titanium (oxi)carbonitride with a thickness of from 2 to 3 microns.

16 Claims, 1 Drawing Figure

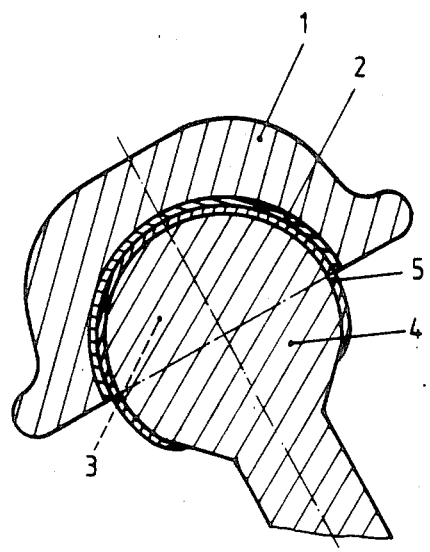

JOINT IMPLANT

RELATED APPLICATIONS

This application is a continuation-in-part of application Ser. No. 419,185 filed Sept. 17, 1982, now U.S. Pat. No. 4,522,453, which in turn is a continuation of application Ser. No. 180,578 filed Aug. 25, 1980, now abandoned, which in turn is a continuation of application Ser. No. 24,421 filed Mar. 27, 1979, now abandoned. The disclosure of application Ser. No. 24,421 filed Mar. 27, 1979 is hereby expressly incorporated by reference.

BACKGROUND OF THE INVENTION

The present invention relates to a joint implant. More particularly, the present invention relates to a joint implant having a hard material coating thereon.

As is known, joint implants have frequently been constructed with members having mutually sliding surfaces thereon. It has been known to increase the wear resistance and/or corrosion resistance of such surfaces by providing protective layers on these surfaces. It has now been found that the material or materials which have been used for such layers do not meet all requirements, for example, with respect to the sliding properties and/or adhesion properties of the layers on the implant members.

SUMMARY OF THE INVENTION

Accordingly, it is an object of the present invention to improve the sliding, wear resistance and adhesion characteristics of the sliding surfaces of a joint implant.

It is another object of the present invention to improve the sliding characteristics of the members of a total prosthesis.

BRIEF DESCRIPTION OF THE DRAWING

The FIGURE is a schematic section of a hip joint prosthesis.

DETAILED DESCRIPTION OF THE PREFERRED EMBODIMENTS

The present invention provides a joint implant which comprises a pair of members. Each of the members has a surface for slidingly engaging the surface of the other member. The surface of each member has a hard material coating thereon. In accordance with the present invention, the hard material is selected from the group consisting of metal carbide, metal nitride and metal carbonitride.

In a first embodiment, one member of the joint implant is provided with a coating of titanium carbide or titanium carbonitride while the other member is provided with a coating of titanium nitride or titanium carbonitride.

The production of the hard material layers on the mutually sliding members may be accomplished by any suitable process, for instance chemical vapor deposition (CVD) or physical vapor deposition (PVD), on a highly polished surface of the sliding member. In this regard, the deposited layers may have a thickness in the range of from 1 to 5 microns.

It has been found that couples of hard material layers, particularly carbide-nitride, carbonitride-nitride and carbonitride-carbonitride pairings, yield good results with respect to wear resistance and adhesion on the implant member. In this regard, the joint implant member or substrate preferably consists of a metal in which at least one of iron, cobalt and titanium is contained at least as the base material. Naturally, the substrate may also be made of other materials commonly used in implant technology, such as a plastic or a pure metal such as titanium.

In a second embodiment, the joint implant may be in the form of a total hip joint prosthesis. The total hip joint prosthesis includes a socket bowl having a sliding surface with a titanium nitride or a titanium carbonitride coating and an articular head having a sliding surface with a titanium carbonitride or titanium carbide coating.

In a third embodiment, the socket bowl having a sliding surface is provided with a titanium oxinitride or titanium oxicarbonitride coating and the articular head is provided with a titanium carbonitride or titanium carbide coating.

In a fourth embodiment, the socket bowl is provided with a titanium nitride or titanium carbonitride coating and the articular head is provided with a titanium oxicarbonitride or titanium oxicarbide coating.

By way of example, a socket bowl of a metal hip joint socket having a cobalt-chromium-molybdenum (CoCrMo) base may be provided, by any suitable manufacturing technique, with a titanium (oxi)carbonitride or titanium (oxi)nitride layer having a thickness of from 2 to 3 microns after the surface of the bowl has been highly polished, for example to a roughness class N4 or better. The roughness class N4 of a surface is defined by a coefficient RA, the value of which is equal to 8 microinches or 0.2 micrometer. The coefficient RA (according to ISO terminology) represents the arithmetic mean of the departures of the profile of the surfaces from the mean line.

In the same manner, the articular head of a femur part of the hip joint prosthesis is highly polished to the same quality class and, thereafter, provided with a titanium (oxi)carbonitride or a titanium (oxi)carbide layer also having a thickness of from 2 to 3 microns. These two parts yield a total prosthesis having good sliding properties and firmly adhering hard material coatings on the sliding surfaces thereof. The FIGURE schematically shows a section of a total hip joint prosthesis; the socket 1 thereof is made of a CoCrMo-alloy which is generally used for implants in the human body. The sliding surface of socket bowl 3 is provided with a layer 2 of titanium nitride or titanium carbonitride which is, for example, about 3 microns thick.

Similarly, the corresponding surface of the articular head 4 is coated with a sliding layer 5 of titaniun carbide or titanium carbonitride which has a thickness of, for example, about 4 microns. The articular head itself is made of the same CoCrMo-alloy as the socket 1.

While the present invention has been described in detail and with reference to specific examples thereof, it will be apparent to one skilled in the art that various changes and modification can be made therein without departing from the spirit and scope thereof.

What is claimed is:

1. A tribological system comprising a first and second member, which together comprise a joint implant, each said member having a surface, said surface of said first member slidingly engaging said surface of said second member, a hard material coating on each of said surfaces, said hard material coating on said first member being titanium carbonitride, and said hard material coating on said second member being selected from the group consisting of titanium carbide, titanium nitride and titanium carbonitride.

2. A tribological system according to claim 1, wherein each said hard material coating has a thickness of from 1-5 microns.

3. A tribological system according to claim 1, wherein at least one of said first and second members comprises a metal selected from the group consisting of iron, cobalt and titanium.

4. A tribological system according to claim 1, wherein said first member comprises a socket bowl, said second member comprises an articular head and said articular head slidingly engages said socket bowl.

5. A tribological system comprising a first and second member, which together comprise a joint implant, each said member having a surface, said surface of said first member slidingly engaging said surface of said second member, a hard material coating on each of said surfaces, said hard material coating on said first member being titanium oxicarbide and said hard material coating on said second member being selected from the group consisting of titanium nitride and titanium carbonitride.

6. A tribological system according to claim 5, wherein each said hard material coating has a thickness of from 1-5 microns.

7. A tribological system according to claim 5, wherein at least one of said first and second members comprises a metal selected from the group consisting of iron, cobalt and titanium.

8. A tribological system according to claim 5, wherein said first member comprises a socket bowl, said second member comprises an articular head and said articular head slidingly engages said socket bowl.

9. A tribological system comprising a first and second member, which together comprise a joint implant, each said member having a surface, said surface of said first member slidingly engaging said surface of said second member, a hard material coating on each of said surfaces, said hard material coating on said first member being selected from the group consisting of titanium carbide and titanium carbonitride, and said hard material coating on said second member being selected from the group consisting of titanium oxinitride and titanium oxicarbonitride.

10. A tribological system according to claim 9, wherein each said hard material coating has a thickness of from 1-5 microns.

11. A tribological system according to claim 9, wherein at least one of said first and second members comprises a metal selected from the group consisting of iron, cobalt and titanium.

12. A tribological system according to claim 9, wherein said first member comprises a socket bowl, said second member comprises an articular head and said articular head slidingly engages said socket bowl.

13. A tribological system comprising a first and second member, which together comprise a joint implant, each said member having a surface, said surface of said first member slidingly engaging said surface of said second member, a hard material coating on each of said surfaces, said hard material coating on said first member being selected from the group consisting of titanium oxicarbide and titanium oxicarbonitride, and said hard material coating on said second member being selected from the group consisting of titanium oxinitride and titanium oxicarbonitride.

14. A tribological system according to claim 13, wherein each said hard material coating has a thickness of from 1-5 microns.

15. A tribological system according to claim 13, wherein at least one of said first and second members comprises a metal selected from the group consisting of iron, cobalt and titanium.

16. A tribological system according to claim 13, wherein said first member comprises a socket bowl, said second member comprises an articular head and said articular head slidingly engages said socket bowl.

* * * * *